United States Patent [19]

Kluge et al.

[11] Patent Number: 5,049,497
[45] Date of Patent: Sep. 17, 1991

[54] NOVEL PROCESS FOR THE SYNTHESIS OF THE ENANTIOMERS OF BICYCLO(4.2.0)OCT-2-EN-7-ONE AND DERIVATIVES

[75] Inventors: Arthur F. Kluge, Los Altos; Dennis J. Kertesz, Palo Alto, both of Calif.

[73] Assignee: Syntex (U.S.A.) Inc., Palo Alto, Calif.

[21] Appl. No.: 900,029

[22] Filed: Aug. 25, 1986

[51] Int. Cl.⁵ .......................... C12P 7/26; C12P 7/24; C12P 7/02; C12P 7/00

[52] U.S. Cl. ................................. 435/148; 435/147; 435/155

[58] Field of Search ............... 435/156, 280, 942, 155, 435/132; 568/374, 157, 155, 148

[56] References Cited

U.S. PATENT DOCUMENTS 4,130,721 12/1978 Bundy et al. .

OTHER PUBLICATIONS

Bucciarelli et al., "Asymmetric Reduction of Trifluoromethyl and Methyl Ketone by Yeast; An Improved Method", Synthesis, vol. 11, 897–899, 1983.
Nakamura et al., "Stereochemical Control in Yeast Reduction", Tet. Lett., vol. 25, 3979–3982, 1984.
Davies et al, "Reduction of 7-Chlorobicyclo[3.2.0]Hept-en-6-one Catalysed by 32, 20β-Hydroxysteroid Dehydrogenase", Tetrahedron Lett. vol. 27, 1093–1094, 1986.
March, Advanced Organic Chemistry, "Oxidations and Reductions", pp. 1048–1120, 1985.
Fersht, "Stereochemistry of Enzymatic Reactions" in Enzyme Structure and Mechanism, pp. 221–247, W. H. Freeman and Company, 1985.
Mori et al., "A New Syntheiss of (+)-6a-Carbaprostaglandin Iz Employing Yeast Reduction of a β-Keto Ester Derived from cis-Bicyclo[3.3.0]Octane-37,-Dione as the Key Step", Tetrahedron, vol. 42, 435–444, 1986.
Newton et al., "Substrate Non-Enantiospecific and Product Enantioselective Reduction of Bicylo9[3.2.0-]Hept-2-en-6-one using Yeast" J.C.S. Chem. Comm., pp. 908–909, 1979.

Primary Examiner—Elizabeth C. Weimar
Assistant Examiner—Gail Poulos
Attorney, Agent, or Firm—Brian Lewis; David A. Lowin; Tom M. Moran

[57] ABSTRACT

The enantiomers of formulas

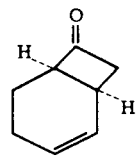 (1)

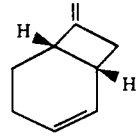

(2)

are prepared in a sequence starting from the racemic compound of formula

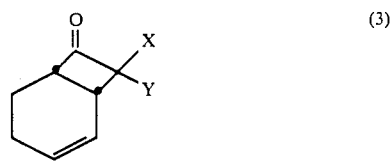 (3)

wherein X is hydro or bromo when Y is bromo, or X is chloro when Y is chloro. The key step of this process involves a microbial reduction of the compound of formula (3) to give a ketone and an alcohol of high enantiomeric purity.

31 Claims, No Drawings

NOVEL PROCESS FOR THE SYNTHESIS OF THE ENANTIOMERS OF BICYCLO(4.2.0)OCT-2-EN-7-ONE AND DERIVATIVES

BACKGROUND OF THE INVENTION

1. Field of the Invention

This invention relates to a novel process for the synthesis of both enantiomers of bicyclo[4.2.0]oct-2-en-7-one and intermediates therefor and their application to the synthesis of certain bicyclo[4.2.0]octane derivatives, useful for treating cardiovascular disorders.

2. Related Disclosures

A method for the synthesis of certain bicyclo[4.2.0]octane derivatives, useful for treating cardiovascular disorders, was disclosed in U.S. patent application Ser. No. 716,872, which is incorporated herein by reference. Three steps of this method involved separation of isomers from a diastereomeric mixture by (1) formation of a cobalt complex, (2) separation of this complex by chromatography and (3) conversion of the separated cobalt diastereomers back to the uncomplexed isomers.

It would be valuable to have a process for the preparation of the bicyclo[4.2.0]octane derivatives useful for treating cardiovascular disorders that did not involve the above three steps. A novel process has been discovered that achieves this end, by starting from resolved bicyclo[4.2.0]oct-2-en-7-one.

Subject matter related to the process of our invention is disclosed in U.S. Pat. No. 4,130,721, Tet. Lett., 1093-1094, 1986 and J.C.S. Chem. Comm., 908-909, 1979.

SUMMARY OF THE INVENTION

The present invention is a novel process for the preparation of the enantiomers represented by the formulas:

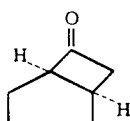
(1)

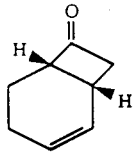
(2)

from the compound

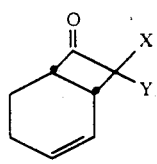
(3)

wherein X is hydro or bromo when Y is bromo, or X is chloro when Y is chloro.

More particularly, the present invention is a process for such conversion. Namely (a) microbial reduction of the compound of formula (3) to give a mixture represented by the formulas

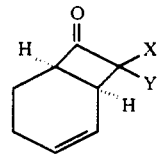
(4)

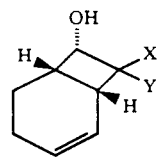
(5)

(b) separation of the compounds of formulas (4) and (5),
(c) oxidation of the alcohol of formula (5) to the ketone represented by the formula

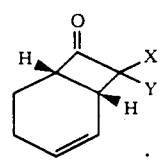
(7)

and (d) dehalogenation of the compounds of formulas (4) and (7) to give the compounds represented by the formulas (1) and (2), respectively. In particular, the key step of reducing the compound of formula (3) microbially gives the surprising result of rapidly reducing only one enantiomer of (3) to give an alcohol of very high optically purity, the compound of formula (5), while leaving the other enantiomer, the compound of formula (4), unreacted and also of very high optical purity. This is an unexpectedly superior result when compared with attempts to separate the enantiomers conventionally, for example, by first preparing diastereomeric ketals or oxazolidines, by reaction with optically active reagents, of a compound of formula (3) and crystallizing the diastereomers apart in a tedious multi-recrystallization process. This is also an unexpectedly superior result when compared with the microbial reduction of other ketones, since the microbial reduction of our invention is exceptionally rapid and, as only one enantiomer is reduced, the products are easily separated. Another unexpectedly superior result is that the alcohols, the compounds of formulas (5) and (6), are solids and thus can be recrystallized to give maximum optical purity, leading to the desired products of formulas (1) and (2) in a 100% enantiomerically pure form. The result of obtaining rapid microbial reduction of only one enantiomer is associated with the stereoelectronic effects of the bulky halogen substituents at the 8-position.

Another aspect of the present invention is the process for the preparation of both enantiomers represented by the formulas (1) and (2) as 100% optically pure isomers. Namely (a) microbial reduction of the compound of formula (3) to give a mixture represented by the formulas

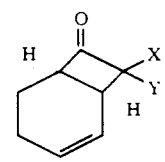
(4)

$$\underset{\text{(5)}}{\text{[structure: OH, H, X, Y, H on bicyclic ring with double bond]}}$$

wherein X is hydro or bromo when Y is bromo, or X is chloro when Y is chloro. (b) separation of the compounds of formulas (4) and (5), (c) reduction of the compound of formula (4) to give the compound of the formula:

$$\underset{\text{(6)}}{\text{[structure: OH, H, X, Y, H on bicyclic ring with double bond]}}$$

(d) optional purification of the compounds of formulas (6) and (5) by recrystallization, (e) oxidation of the compounds of formulas (6) and (5) to the compounds of formula:

$$\underset{(4)}{\text{[ketone structure]}} \quad \text{and} \quad \underset{(7)}{\text{[ketone structure]}}$$

respectively, and (f) dehalogenation of the compounds of formulas (4) and (7) to the compounds of formula (1) and (2).

Yet another aspect of the present invention is a compound represented by the formula (4), (5) (6) or (7), wherein X is hydro or bromo when Y is bromo, or X is chloro when Y is chloro.

DETAILED DESCRIPTION AND PRESENTLY PREFERRED EMBODIMENTS OF THE INVENTION

Definitions

The term "alkyl" refers to and includes saturated branched and straight chain hydrocarbon radicals containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

"Cycloalkyl" as used herein means a saturated monocyclic hydrocarbon radical containing 3-8 carbon atoms, such as cyclopropyl, cyclobutyl, cyclopentyl, cyclohexyl, cycloheptyl and cyclooctyl.

The term, "lower alkyl" refers to a branched or unbranched saturated hydrocarbon chain of 1-4 carbons, such as, for example, methyl, ethyl, n-propyl, i-butyl and the like.

The term "alkoxy" refers to the radical —O-alkyl wherein "alkyl" is as defined above. This includes radicals such as methoxy, ethoxy, 2-propoxy, butoxy, 3-pentoxy and the like.

"Lower alkoxy" means the group —OR wherein R is lower alkyl as herein defined.

"Halo" as used herein denotes fluoro, chloro, bromo, or iodo.

"Phenyl" as used herein encompasses all possible isomeric phenyl radicals optionally monosubstituted with a substituent selected from the group consisting of lower alkyl, lower alkoxy, hydroxy, trifluoromethyl and halogen.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

"Microbial reduction" is intended to encompass any reduction carried out by a micro-organism, or a preparation derived from a micro-organism, such as yeasts, yeast extracts, enzymes, dehydrogenases and the like.

"Bakers Yeast" is the common term for Saccharomyces cerevisiae.

The numbering system for the bicyclo[4.2.0]octane system shown in the scheme illustration below is used in naming the intermediates and product compounds of the invention.

[bicyclo[4.2.0]octane numbering diagram]

The absolute stereochemistry at carbons 1 and 6 are specified according to the Cahn-Ingold-Prelog R-S system. When the compound is a pure enantiomer, the stereochemistry at each chiral carbon is specified by either R or S. When a compound is a racemic mixture the stereochemistry at each chiral carbon is specified by either RS or SR, by reference to a single enantiomer of the racemate. In this manner relative stereochemistry is conveyed unambiguously.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, distillation or a combination of these procedures. Specific illustrations are described in the Examples. However, other equivalent separation or purification procedures can be used.

Utility

The compounds of formula (1) and (2) prepared by the present process are utilized in the preparation of certain bicyclo[4.2.0]octane derivatives, useful for treating cardiovascular diseases, represented by the formulas:

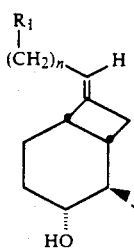 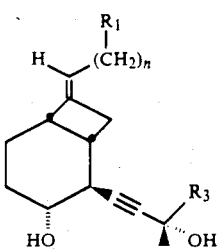

(8) (9)

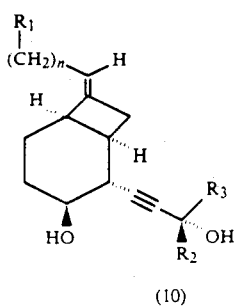

(10)

wherein:
n is 2 or 3;
$R_1$ is $CH_2OH$, CHO, $CO_2R$ or $CO_2H$;
$R_2$ is hydrogen or methyl; and
$R_3$ is linear or branched alkyl having 5-10 carbon atoms,

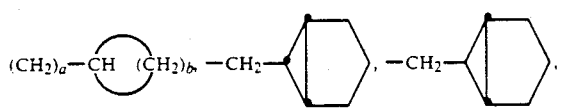

or $-(CH_2)_m$-phenyl optionally substituted with lower alkyl, lower alkoxy, trifluoromethyl, or halogen, in which
a is 0, 1 or 2;
b is 3-7;
m is 1 or 2; and
R is

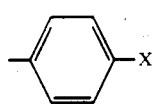

wherein X is

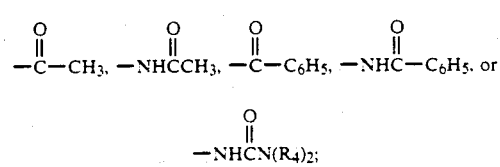

in which each $R_4$ is independently hydrogen or lower alkyl having 1-6 carbon atoms by a process comprising
(a) reaction of the ketones of the formulas (1) and (2) with ethylene glycol to give compounds of the formulas:

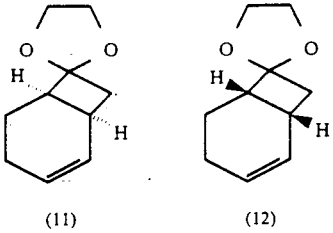

(11) (12)

(b) epoxidizing the compounds of formulas (11) and (12) to give compounds of the formulas:

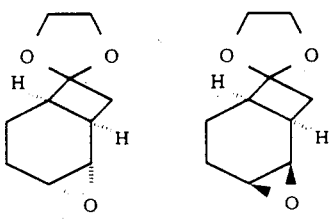

(13) (14)

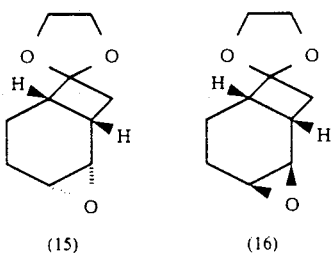

(15) (16)

as a mixture of (13) and (14) or a mixture of (15) and (16) respectively;
(c) treating the mixture of epoxides with a compound of the formula:

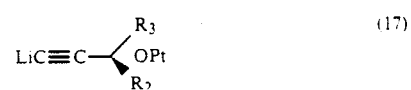

where Pt is a protecting group, in the presence of boron trifluoride to give compounds of the formulas

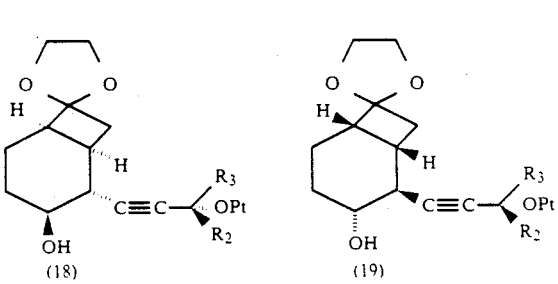

(18) (19)

(d) treating the compounds of formulas (18) and (19) with an acid to give compounds of the formulas

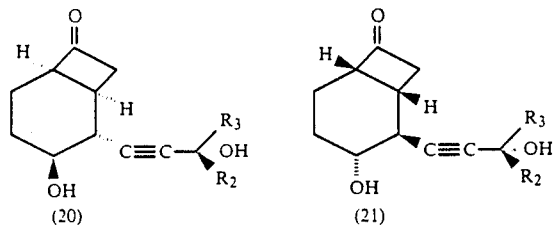

(e) reacting the compounds of formulas (20) or (21) with a phosphorus ylid (Wittig reagent) to give a mixture of the compounds of formulas (8) and (9) or (10) and the (E)-isomer corresponding to (10), and (f) separating the individual isomers of (8), (9) and (10).

The present process is illustrated in more detail in the following reaction scheme.

REACTION SCHEME 1

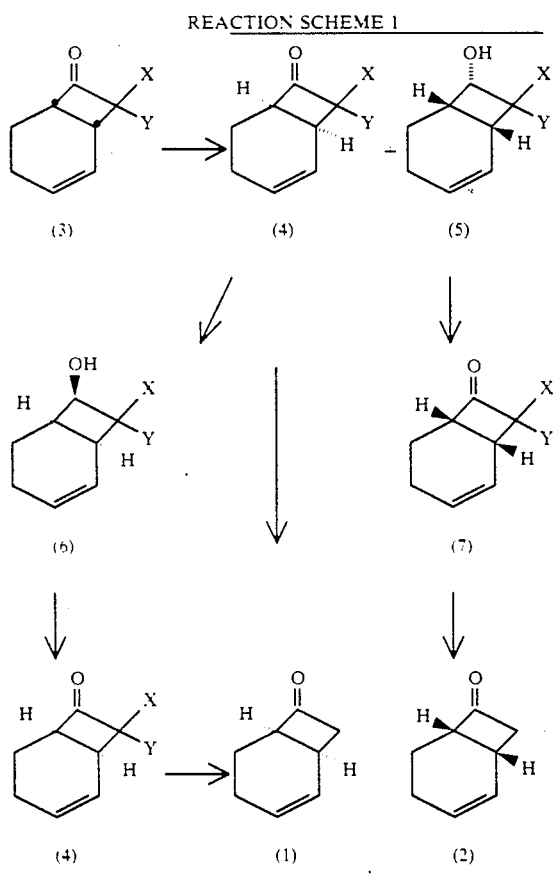

In the first step, the racemic 8-monobromo or 8,8-dihalobicyclo[4.2.0]oct-2-en-7-one (3), preferably 8,8-dichlorobicyclo[4.2.0]oct-2-en-7-one, is treated with a micro-organism, preferably Baker's Yeast, optionally in the presence of a yeast nutrient and a sugar, such as glucose, dextrose or preferably sucrose. For every gram of ketone about 2–25 g, preferably about 8–15 g, of Baker's Yeast is used, plus about 0 g to 1.0 g, preferably about 0.7 g, of yeast nutrient, and about 0 g to 2.0 g, preferably about 0.5 g, of sucrose. The reaction is carried out in a solvent of a lower alcohol and water, such as about 2% to 10% ethanol, preferably about 5% ethanol, in water at a temperature of about 20°–40° C., preferably about 33° C., for about 15 minutes to 2 hours, preferably about 45 minutes. The ketone (4) and the alcohol (5) are isolated, separated and purified by conventional means, preferably by column chromatography.

The ketone of formula (4) may optionally be reduced to the alcohol of formula (6) with a mild reducing agent then recrystallized from a suitable solvent and oxidized back to the compound of formula (4). This process acts as a purification procedure for the compound of formula (4), and results in a compound of 100% enantiomeric purity. For example, the ketone of formula (4) is reacted with about 1 to 10 molar equivalents, preferably about 2 to 4 molar equivalents, of sodium borohydride in a protic solvent such as water, ethanol or preferably methanol at a temperature of about 0°–25° C., preferably about 5° C., for about 15 minutes to 4 hours, preferably about 1 hour, giving the compound of Formula (6), which is isolated and purified by conventional means, preferably recrystallization.

The alcohols of formula (5) and (6) are then converted to the ketones of formula (7) and (4), respectively, using an oxidizing agent such as an aqueous solution of chromic acid and sulfuric acid (Jones reagent), sodium dichromate or an organic chromium reagent, preferably pyridinium chlorochromate. Typically, the ketone is reacted with about 1.5 to 4 molar equivalents, preferably about 2 molar equivalents, of pyridinium chlorochromate in the presence of about 4 to 10 molar equivalents, preferably about 6 molar equivalents, of magnesium sulfate in an inert solvent such as chloroform or preferably methylene chloride. The reaction is carried out at a temperature of about 30°–70° C., preferably about 45° C., for about 2 to 10 hours, preferably about 4 hours. When the reaction is substantially complete, the products are isolated and purified by conventional means.

The haloketones of formulas (4) and (7) are then dehalogenated to the unsubstituted enantiomeric ketones of formulas (1) and (2) with a mild dehalogenating agent, for example, tributyltin hydride, a zinc-copper couple or preferably zinc in acetic acid. Typically, the dichloroketone is dissolved in an organic carboxylic acid, preferably acetic acid and reacted with about 2 to 10 molar equivalents, preferably about 5 molar equivalents, of zinc dust at a temperature of about 50°–70° C., preferably about 70° C., for about 20 minutes to 2 hours, preferably about 1 hour. A further quantity of zinc, about 2 molar equivalents, is then added and the mixture heated at about 70°–100° C., preferably about 75° C., for about 20 minutes to 2 hours, preferably about 1 hour. When the reaction is substantially complete the products of formula (1) and (2) are isolated and purified by conventional means.

The above reaction scheme demonstrates the preferred reaction sequence for the conversion of the compounds of formula (4) and (5) to the compounds of formula (1) and (2) respectively. It is obvious that several alternate reaction pathways also arrive at the compounds of formula (1) and (2). Some alternate routes are illustrated below in Reaction Scheme 2, using the compound of formula (5) where X and Y are chlorine as an example.

REACTION SCHEME 2

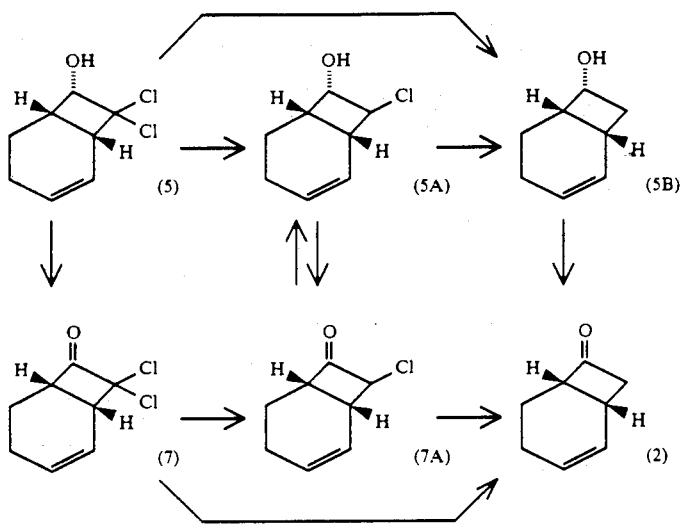

For example, treatment of the compound of formula (5) with a dehalogenating agent, for example tri-n-butyltin hydride, for a brief period of time gives the monochloro compound of formula (5A). Treatment of the compounds of formula (5) or (5A) with, for example, tri-n-butyltin hydride at elevated temperatures and prolonged reaction time gives the compound of formula (5B), which is then oxidized as shown in Reaction Scheme 1 to give the desired compound of formula (2).

The compound of formula (7), obtained by oxidation of the compound of formula (5) as shown in Reaction Scheme 1 above, may in the same manner be first converted to the monochloro compound of formula (7A) by treatment with a dehalogenating agent, for example zinc in acetic acid, for a short period of time at room temperature. Treatment of the compounds of formula (7) or (7A) with zinc in acetic acid at elevated temperatures, as shown in Reaction Scheme 1, gives the desired compound of formula (2). It should also be noted that the compounds of formula (5A) and (7A) are interconvertible by standard oxidation and reduction reactions.

Similarly, starting with the compound of formula (4) and reducing it to the compound of formula (6), as shown in Reaction Scheme 1, the same synthetic pathways as shown in Reaction Scheme 2 may be applied to arrive at the compound of formula (1). Similarly, the same reaction sequences apply for compounds of formula (4) and (5) where X and Y are bromo, or where X is hydro and Y is bromo.

Preparation of Starting Materials

The compound of formula (3) where X and Y are each chloro or bromo, is made by reaction of 1,3-cyclohexadiene and the appropriate dihaloacetyl chloride. The reaction is discussed in more detail in *Tetrahedron* 27:615, (1971), which is incorporated herein by reference, wherein the product of the reaction is the cis-configuration as the ring junction.

The phosphorous ylides (Wittig reagents) are prepared by procedures well known in the chemical arts. For example, reaction of the appropriate ω-halocarboxylic acid with triphenylphosphine to give the corresponding triphenyl phosphonium salt, which is reacted with a base. The reaction is discussed in more detail in *J. Org. Chem.* 27, 3404 (1962), which is incorporated herein by reference.

The chiral acetylenic alcohols used to prepare the salt of formula (17) are prepared by reducing the appropriate acetylenic ketone with a chiral reducing agent, for example, (S)-8-isopinocamphenyl-9-borabicyclo[3.3.1-]nonane. Alternatively, the racemic acetylenic alcohols are converted to a hemiphthalate and the diastereomeric salts formed with an optically active amine separated by recrystallization. These reactions are discussed in more detail in U.S. patent application Ser. No. 716,872, which is incorporated herein by reference.

Preferred Embodiments

One preferred embodiment of the present invention includes the process whereby the micro-organism is Baker's Yeast. A more preferred embodiment includes the process whereby X and Y are both chloro. Another more preferred embodiment includes the process whereby the oxidizing agent is pyridinium chlorochromate. Yet another more preferred embodiment includes the process whereby the dehalogenating agent is zinc in acetic acid. A most preferred embodiment includes the process whereby the compounds of formula (5) and (6) are recrystallized to give 100% pure enantiomers.

The following examples serve to illustrate the invention. They should not be construed as in any way narrowing or limiting the scope of the invention as claimed.

EXAMPLE 1

Preparation of
(1S,6R)-8,8-dichlorobicyclo[4.2.0]oct-2-en-7-one and
(1R,6S,7S)-8,8-dichlorobicyclo[4.2.0]oct-2-en-7-ol, the
compounds of formula (4) and (5)

A. A mixture of 3 liters of water, 150 g of an active Bakers Yeast, 15 g of edible yeast and 10 g of sucrose were stirred at 32° C. A solution of 24 g of 8,8-dichlorobicyclo[4.2.0]oct-2-en-7-one in 170 ml of ethanol was added dropwise over a 15 minute period, followed by a further 5 g of sucrose. After stirring for 45 minutes the reaction mixture was centrifuged to remove the yeast, which was washed with acetone and the washings combined with the aqueous product from the centrifuge.

The combined product was washed several times with ethyl acetate, the organic washings combined filtered and the solvent removed from the filtrate under reduced pressure. The residue was chromatographed on silica gel, eluting with 5% acetone in hexane, initially and gradually increasing the proportion of acetone to 100%, giving 4.0 g of (1S,6R)-8,8-dichlorobicyclo[4.2.0]oct-2-en-7-one (4) as a liquid, $[\alpha]_D = -78.7°$ (C=0.8, CHCl$_3$), and 8.8 g of crude (1R,6S,7S)-8,8-dichlorobicyclo[4.2.0]oct-2-en-7-ol (5), which was recrystallized from hexane to give 6.4 g of pure (5), m.p.=86°-7° C., $[\alpha]_D = -217.1°$ (C=0.6, CHCl$_3$).

In an alternative work-up procedure to that shown above, an equal volume of acetone was added to the fermentation broth, the solid filtered off through celite, the celite washed with acetone and solvent removed from the filtrate under reduced pressure. The residue was then chromatographed and purified as shown above.

B. Similarly, following the procedure of paragraph 1.A. above, but starting with the compounds of formula (3) where X is hydro or bromo and Y is bromo, the following compounds of formula (4) and (5) are prepared: (1S,6R)-8-bromobicyclo[4.2.0]oct-2-en-7-one, and (1R,6S,7S)-8-bromobicyclo[4.2.0]oct-2-en-7-ol (1S,6R)-8,8-dibromobicyclo[4.2.0]oct-2-en-7-one, and (1R,6S,7S)-8,8-dibromobicyclo[4.2.0]oct-2-en-7-ol

EXAMPLE 2

Preparation of (1S,6R,7R)-8,8-dichlorobicyclo[4.2.0]oct-2-en-7-ol, the compound of formula (6)

A. A solution of 3.0 g of (1S,6R)-8,8-dichlorobicyclo[4.2.0]oct-2-en-7-one, the compound of formula (4), is dissolved in 120 ml of methanol and treated at 0° C. with 1.2 g of sodium borohydride, and the mixture is stirred at 25° C. for 1 hour. The solvent is removed under reduced pressure and the residue partitioned between methylene chloride and water. The extract is dried over anhydrous sodium sulfate, filtered and the solvent removed under reduced pressure. The residue is recrystallized from hexane to give (1S,6R,7R)-8,8-dichlorobicyclo[4.2.0]oct-2-en-7-ol, $[\alpha]_D = +214.4°$ (CHCl$_3$).

B. Similarly, following the procedure in paragraph 2.A. above, but substituting other ketones from Example 1 for (1S,6R)-8,8-dichlorobicyclo[4.2.0]oct-2-en-7-one, the following compounds of formula (6) are prepared: (1S,6R,7R)-8,8-dibromobicyclo[4.2.0]oct-2-en-7-ol (1S,6R,7R)-8-bromobicyclo[4.2.0]oct-2-en-7-ol

EXAMPLE 3

A. Preparation of (1R,6S)-8,8-dichlorobicyclo[4.2.0]oct-2-en-7-one, the compound of formula (7)

A mixture of 3.9 g of (1R,6S,7S)-8,8-dichlorobicyclo[4.2.0]oct-2-en-7-ol, prepared as shown in Example 1, 9.0 g of pyridinium chlorochromate and 14 g of magnesium sulfate in 200 ml of methylene chloride under nitrogen was refluxed for 4 hours. The mixture was cooled, filtered first through celite then Florisil. Solvent was removed from the eluate under reduced pressure and the residue distilled under vacuum to give 3.1 g of (1R,6S)-8,8-dichlorobicyclo[4.2.0]oct-2-en-7-one, $[\alpha]_D = +71.4°$, (C=0.7, CHCl$_3$).

B. Similarly, starting from (1S,6R,7R)-8,8-dichlorobicyclo[4.2.0]oct-2-en-7-ol, prepared as shown in Example 2, and following the procedure of paragraph 3.A. above, (1S,6R)-8,8-dichlorobicyclo[4.2.0]oct-2-en-7-one is prepared.

C. Similarly, following the procedure in paragraph 3.A. above, but starting with the compounds of formula (5) or (6), prepared as shown in Examples 1 and 2, the following compounds of formula (4) and (7) are prepared: (1S,6R)-8,8-dibromobicyclo[4.2.0]oct-2-en-7-one (1S,6R)-8-bromobicyclo[4.2.0]oct-2-en-7-one (1R,6S)-8,8-dibromobicyclo[4.2.0]oct-2-en-7-one (1R,6S)-8-bromobicyclo[4.2.0]oct-2-en-7-one

EXAMPLE 4

Preparation of (1R,6S)-bicyclo[4.2.0]oct-2-en-7-one

A. To a solution of 1.1 g (1R,6S)-8,8-dichlorobicyclo[4.2.0]oct-2-en-7-one, prepared as shown in Example 3A, in 10 ml of glacial acetic acid was added 2.0 g of zinc dust in portions over a period of 15 minutes. The mixture was then stirred at 65° C. for 1 hour, then a further 0.5 g of zinc dust was added and the mixture stirred at 75° C. for 1 hour. The mixture was cooled, filtered, the solid washed with hexane, the filtrate and combined washings diluted with water and extracted with hexane. The hexane layer was dried over anhydrous sodium sulfate, the solvent removed under reduced pressure and the residue distilled under vacuum to give 500 mg of (1R,6S)-bicyclo[4.2.0]oct-2-en-7-one, the compound of formula (2), $[\alpha]_D = +171.4°$, (C=0.5, CHCl$_3$).

B. Similarly, starting from (1R,6S)-8-bromobicyclo[4.2.0]oct-2-en-7-one or (1R,6S)-8,8-dibromobicyclo[4.2.0]oct-2-en-7-one and following the procedure of paragraph 4.A. above, the compound of formula (2) is prepared.

C. Similarly, starting from (1S,6R)-8,8-dichlorobicyclo [4.2.0]oct-2-en-7-one or (1S,6R)-8,8-dibromobicyclo[4.2.0]oct-2-en-7-one or (1S,6R)-8-bromobicyclo[4.2.0]oct-2-en-7-one, and following the procedures of paragraph 4.A. above, the corresponding compound of formula (1) is made, (1S,6R)-bicyclo[4.2.0]oct-2-en-7-one.

What is claimed is:

1. A process for preparing a bicyclo[4.2.0]octane derivative, which process comprises:
contacting a racemic bicyclo[4.2.0]octane derivative of the formula

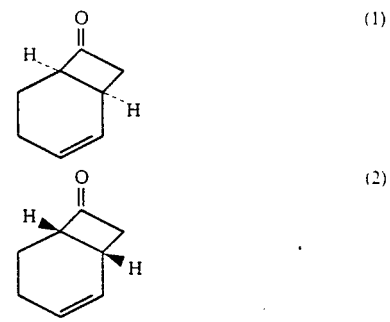

wherein X is hydro or bromo when Y is bromo, or X is chloro when Y is chloro, with Baker's Yeast under conditions sufficient to give a mixture of compounds represented by the formulas

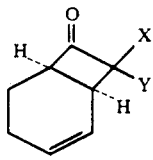

(4)

and

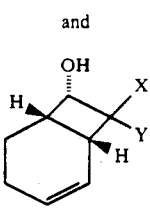

(5)

2. The process of claim 1 wherein the compound represented by the formula (4) is separated from the compound represented by the formula (5)

3. The process of claim 2 wherein X and Y are each chloro.

4. The process of claim 3 which further comprises contacting the compound represented by the formula (4) with a mild reducing agent to give a compound represented by the formula:

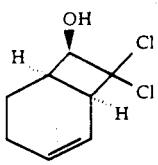

(6)

and (b), optionally recrystallizing the compound represented by the formula (4) from a suitable solvent.

5. The process of claim 4 wherein the reducing agent is sodium borohydride.

6. The process of claim 4 which further comprises contacting the compound represented by the formula (6) with a suitable oxidizing agent to form a compound represented by the formula (4).

7. The process of claim 6 wherein the oxidizing agent is selected from the group consisting of a solution of chromic acid in sulfuric acid, sodium dichromate and an organic chromium reagent.

8. The process of claim 7 wherein the oxidizing agent is pyridinium chlorochromate.

9. The process of claim 6 which further comprises contacting the compound represented by the formula (4) with a dechlorinating agent to give a compound represented by the formula:

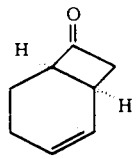

(1)

10. The process of claim 9 wherein the dechlorinating agent is zinc in acetic acid.

11. The process of claim 3 which further comprises contacting the compound represented by the formula (4) with a dechlorinating agent to give a compound represented by the formula (1).

12. The process of claim 11 wherein the dechlorinating agent is zinc in acetic acid.

13. The process of claim 3 which further comprises contacting the compound represented by the formula (5) with a suitable oxidizing agent to form a compound represented by the formula:

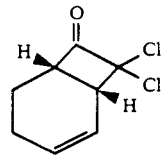

(7)

14. The process of claim 13 wherein the oxidizing agent is selected from the group consisting of a solution of chromic acid in sulfuric acid, sodium dichromate and an organic chromium reagent.

15. The process of claim 14 wherein the oxidizing agent is pyridinium chlorochromate.

16. The process of claim 14 which further comprises contacting the compound represented by the formula (7) with a dechlorinating agent to give a compound represented by the formula:

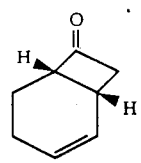

(2)

17. The process of claim 16 wherein the dechlorinating agent is zinc in acetic acid.

18. A process for preparing an individual enantiomer of a bicyclo[4.2.0]octane derivative, which process comprises:
(a) contacting a racemic bicyclo[4.2.0]octane derivative of the formula

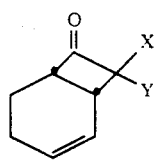

(3)

wherein X is hydro or bromo when Y is bromo, or X is chloro when Y is chloro, with a Baker's Yeast under conditions sufficient to give a mixture of compounds represented by the formulas

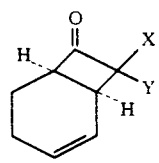

(4)

and

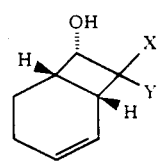

(5)

(b) separating the compound represented by the formula (4) from the compound represented by the formula (5); and
(c) contacting the compound represented by the formula (4) with a dehalogenating agent to give a compound represented by the formula

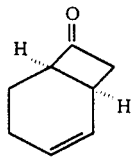
(1)

19. The process of claim 18 wherein X and Y are each chloro.
20. The process of claim 19 wherein the dechlorinating agent is zinc in acetic acid.
21. A process for preparing an individual enantiomer of a bicyclo[4.2.0]octane derivative, which process comprises:
   (a) contacting a racemic bicyclo[4.2.0]octane derivative of the formula

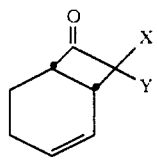
(3)

wherein X is hydro or bromo when Y is bromo, or X is chloro when Y is chloro, with Baker's Yeast under conditions sufficient to give a mixture of compounds represented by the formulas

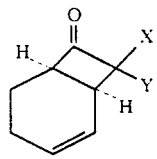
(4)

and

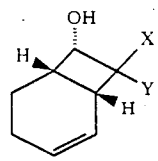
(5)

(b) separating the compound represented by the formula (4) from the compound represented by the formula (5);
(c) reducing the compound represented by the formula (4) with a mild reducing agent to give a compound represented by the formula

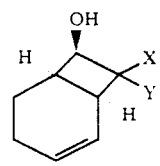
(6)

(d) optionally recrystallizing the compound represented by the formula (6) from a suitable solvent
(e) oxidizing the compound represented by the formula (6) to a compound represented by the formula (4); and
(f) contacting the compound represented by the formula (4) with a dehalogenating agent to give a compound represented by the formula (1):

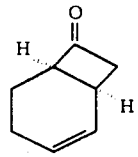
(1)

22. The process of claim 21 wherein X and Y are each chloro.
23. The process of claim 22 wherein in step (c) the reducing agent is sodium borohydride.
24. The process of claim 22 wherein in step (e) the oxidizing agent is selected from the group consisting of a solution of chromic acid in sulfuric acid, sodium dichromate and an organic chromium reagent.
25. The process of claim 24 wherein the oxidizing agent is pyridinium chlorochromate.
26. The process of claim 22 wherein in step (f) the dechlorinating agent is zinc in acetic acid.
27. A process for preparing an individual enantiomer of a bicyclo[4.2.0]octane derivative, which process comprises:
   (a) contacting a racemic bicyclo[4.2.0]octane derivative of the formula

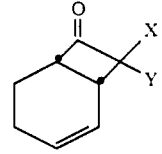
(3)

wherein X is hydro or bromo when Y is bromo, or X is chloro when Y is chloro, with Baker's Yeast under conditions sufficient to give a mixture of compounds represented by the formulas

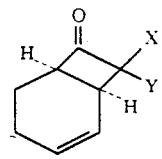
(4)

and

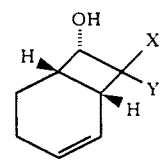
(5)

(b) separating the compound represented by the formula (4) from the compound represented by the formula (5);
(c) optionally recrystallizing the compound represented by the formula (5) from a suitable solvent (d) contacting the compound represented by the formula (5) with a suitable oxidizing agent to form a compound represented by the formula

 (7)

and (e) contacting the compound represented by the formula (7) with a dehalogenating agent to give a compound represented by the formula (2).

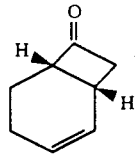 (2)

28. The process of claim 27 wherein X and Y are each chloro.

29. The process of claim 28 wherein in step (d) the oxidizing agent is selected from the group consisting of a solution of chromic acid in sulfuric acid, sodium dichromate and an organic chromium reagent.

30. The process of claim 29 wherein the oxidizing agent is pyridinium chlorochromate.

31. The process of claim 28 wherein in step (e) the dechlorinating agent is zinc in acetic acid.

* * * * *